US011154094B2

(12) United States Patent
Carroll et al.

(10) Patent No.: US 11,154,094 B2
(45) Date of Patent: Oct. 26, 2021

(54) AEROSOL GENERATING DEVICE AND CAPSULE

(71) Applicant: JT International SA, Geneva (CH)

(72) Inventors: James Thomas Carroll, Dublin (IE); Lyndsey Alice Bryce, Dublin (IE); Christopher William Murphy, Dublin (IE)

(73) Assignee: JT International S.A.

( * ) Notice: Subject to any disclaimer, the term of this patent is extended or adjusted under 35 U.S.C. 154(b) by 177 days.

(21) Appl. No.: 15/575,175

(22) PCT Filed: May 16, 2016

(86) PCT No.: PCT/EP2016/060934
§ 371 (c)(1),
(2) Date: Nov. 17, 2017

(87) PCT Pub. No.: WO2016/184824
PCT Pub. Date: Nov. 24, 2016

(65) Prior Publication Data

US 2018/0140015 A1 May 24, 2018

(30) Foreign Application Priority Data

May 19, 2015 (EP) .................................... 15168224

(51) Int. Cl.
*A24F 40/53* (2020.01)
*A24F 40/485* (2020.01)
(Continued)

(52) U.S. Cl.
CPC ............ *A24F 40/53* (2020.01); *A24F 40/485* (2020.01); *H05B 3/44* (2013.01); *A24F 40/10* (2020.01);
(Continued)

(58) Field of Classification Search
CPC ...... A24F 47/00; A24F 47/008; A24F 47/002; A61M 15/0063; A61M 15/0035; A61M 15/06
See application file for complete search history.

(56) References Cited

U.S. PATENT DOCUMENTS 3,388,838 A 6/1968 Marchant
3,505,870 A 4/1970 Smylie
(Continued)

FOREIGN PATENT DOCUMENTS

EP 1736065 A1 12/2006
EP 2343096 A1 7/2011

OTHER PUBLICATIONS

Extended European Search Report for Application No. EP15168224.2 dated Nov. 16, 2015.
(Continued)

*Primary Examiner* — Alex B Efta
(74) *Attorney, Agent, or Firm* — Lerner, David, Littenberg, Krumholz & Mentlik, LLP

(57) ABSTRACT

There is provided an aerosol generating device and a capsule adapted for use with the aerosol generating device. The aerosol generating device comprises a cavity positioned on one side of the aerosol generating device. The cavity is configured to host a capsule and the capsule is configured to contain an aerosol generating substance. The capsule comprises an external shell arranged to retain an aerosol generating substance and an outlet in the external shell configured to engage with the aerosol generating device when the capsule is retained in the cavity.

12 Claims, 2 Drawing Sheets

Figure 1:
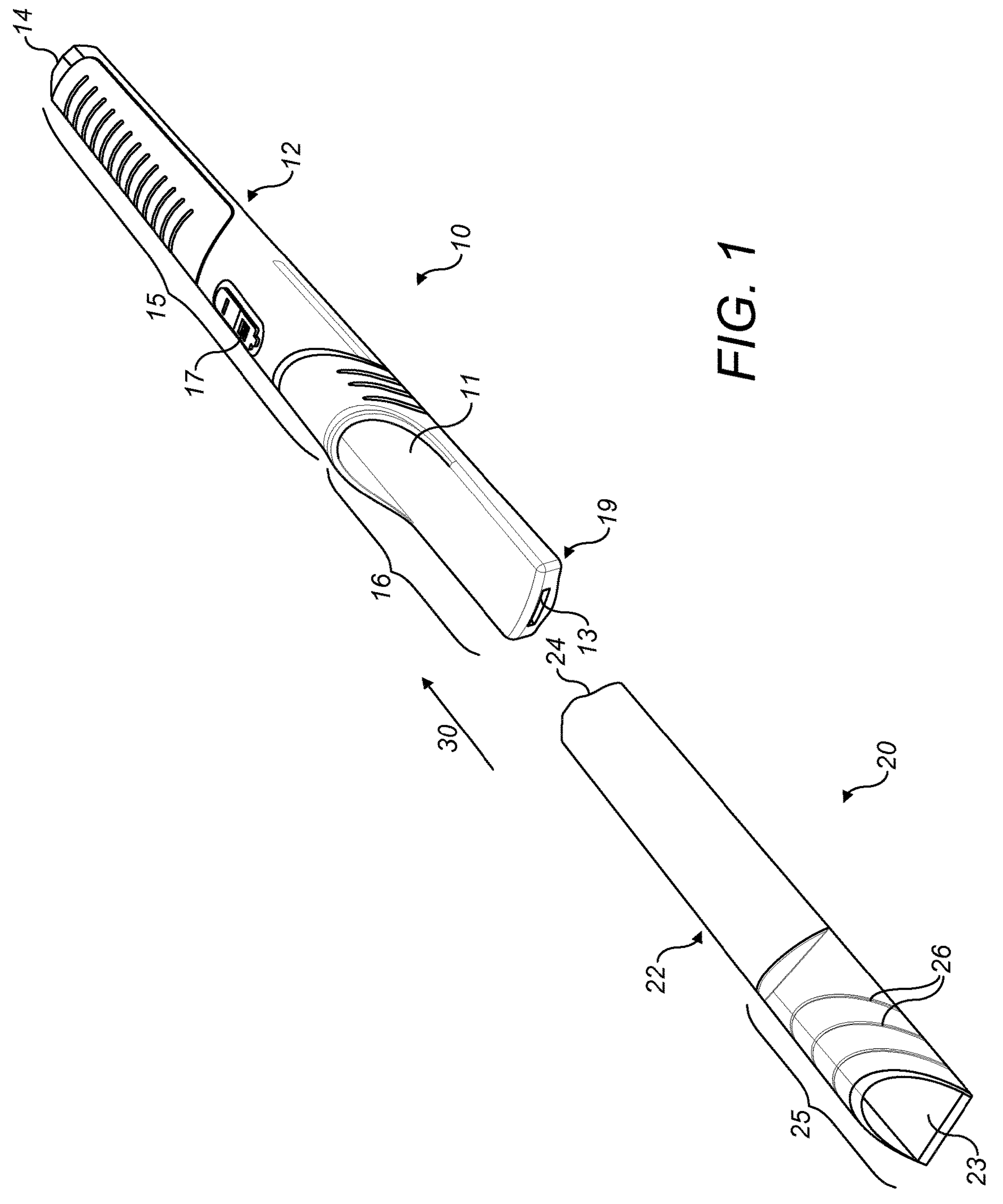

(51) Int. Cl.
*A24F 40/10* (2020.01)
*A24F 40/60* (2020.01)
*A24F 47/00* (2020.01)
*H05B 3/44* (2006.01)

(52) U.S. Cl.
CPC ........ *A24F 40/60* (2020.01); *H05B 2203/021* (2013.01)

(56) References Cited

U.S. PATENT DOCUMENTS

| | | | | |
|---|---|---|---|---|
| 4,708,151 | A | 11/1987 | Shelar | |
| 5,167,242 | A | 12/1992 | Turner et al. | |
| 7,089,934 | B2 | 8/2006 | Staniforth et al. | |
| 8,955,522 | B1 * | 2/2015 | Bowen | A24F 47/008 128/202.21 |
| 9,820,510 | B2 * | 11/2017 | Thomas, Jr. | A61M 11/042 |
| 10,015,990 | B2 * | 7/2018 | Mironov | A24F 47/008 |
| 2012/0174914 | A1 * | 7/2012 | Pirshafiey | A61M 11/041 128/200.14 |
| 2013/0129872 | A1 * | 5/2013 | Kruger | B65D 85/8043 426/115 |
| 2013/0213418 | A1 | 8/2013 | Tucker et al. | |
| 2014/0360517 | A1 * | 12/2014 | Taggart | A24F 47/008 131/329 |
| 2015/0208729 | A1 * | 7/2015 | Monsees | A24F 47/008 131/329 |
| 2016/0143365 | A1 * | 5/2016 | Liu | A61M 15/06 131/329 |
| 2016/0360789 | A1 * | 12/2016 | Hawes | A24F 40/42 |
| 2017/0202265 | A1 * | 7/2017 | Hawes | A24F 47/008 |

OTHER PUBLICATIONS

International Search Report for Application No. PCT/EP2016/060934 dated Jun. 24, 2016.

* cited by examiner

AEROSOL GENERATING DEVICE AND CAPSULE

The present application is a national phase entry under 35 U.S.C. § 371 of International Application No. PCT/EP2016/060934 filed May 16, 2016, published in English, which claims priority from European Patent Application No. 15168224.2 filed May 19, 2015, all of which are incorporated herein by reference.

The present invention relates to an aerosol generating device and a capsule for use with the aerosol generating device.

Aerosol generating devices such as electronic cigarettes are relatively well known and are becoming increasingly popular. The most common operating principle for such electronic cigarettes is to provide a flavoured vapour to a user without burning material. They often comprise an electrically powered heat source and a reservoir of liquid, whereby the vapour is produced by delivering the liquid to the heat source.

Since the liquid is depleted during this process, after a certain amount of use the reservoir is emptied. Accordingly, prior art electronic cigarettes often provide a replaceable cartridge containing the heater and liquid reservoir which may be discarded and replaced when necessary. There are however several on-going problems which such conventional devices.

Firstly, prior art devices often locate the reservoir of aerosol-producing substance inside a removable cartridge such that there is no easy way for a user to determine the amount of aerosol generating substance remaining in the reservoir during use. This may result in continued use of the device after the substance has been depleted, resulting in an unpleasant flavour for the user. It also may result in the cartridge being depleted unexpectedly, at which time it may be difficult for the user to purchase further cartridges to continue use. Therefore there exists a need for a cartridge arrangement which allows for a user to easily determine the amount of aerosol producing substance remaining in the reservoir.

Prior art cartridges are generally configured to screw into one end of the aerosol generating device in order to connect to the battery and other components located in the body. Such an arrangement results in a substantial increase in the dimensions of the device making them large, bulky and awkward to use. The placement of the cartridge at one end of the device also means that this end cannot be utilised for another component such as an opening for a replaceable battery or the mouthpiece.

Some prior art devices seek to solve this problem by providing an aerosol generating device which may be opened to allow replacement of an internal cartridge containing the reservoir. However such an arrangement often requires a cumbersome operation involving the handling of small parts and the exposure of the delicate internal components of the device. Furthermore prior art devices often require that the capsule is screwed into the body, or that components of the body are screwed together after replacement of the internal capsule. After repeated use the screw threads are subject to wear, leading to failure and replacement is required.

There accordingly exists a need for an aerosol generating device and capsule wherein the capsule may be loaded externally in a straightforward operation, without the need to open or unscrew components of the device. There also exists a need for the capsule to remain partially exposed such that a user may gauge the amount of substance remaining in the capsule. Importantly, these benefits must be obtained without the detrimental effect common to prior art external capsules, namely, it must also not substantially increase the dimensions of the device so as to render it cumbersome to use.

The present invention seeks to provide an aerosol generating device and replaceable capsule that may be replaced in a user-friendly manner that overcomes the problems of the prior art.

According to the present invention there is provided an aerosol generating device and a capsule adapted for use with the aerosol generating device. The aerosol generating device comprises: a cavity positioned on one side of the aerosol generating device; wherein the cavity is configured to host a capsule;

and the capsule is configured to contain an aerosol generating substance. The capsule comprises an external shell arranged to retain an aerosol generating substance; and an outlet in the external shell configured to engage with the aerosol generating device when the capsule is retained in the cavity.

With the aerosol generating device and capsule according to the present invention it is possible to provide a means of replenishing an aerosol generating substance by replacing a capsule which does not require any disassembly of the device or unscrewing of components with a straightforward and user-friendly procedure. The capsule is loaded externally but does not substantially increase the dimensions of the device, providing a device which is easy to handle in use. The ends of the device are also left free allowing for use with other components of the device such as a mouthpiece and battery. Furthermore, the capsule remains at least partially external to the device allowing the user to gauge the remaining aerosol generating substance contained within. Utilising a capsule which remains at least partially exposed also allows for a greater proportion of the internal volume of the device to be devoted to storing the battery such that the size (and therefore lifetime) of the battery may be increased without impacting on the overall size of the body.

Figure 2:
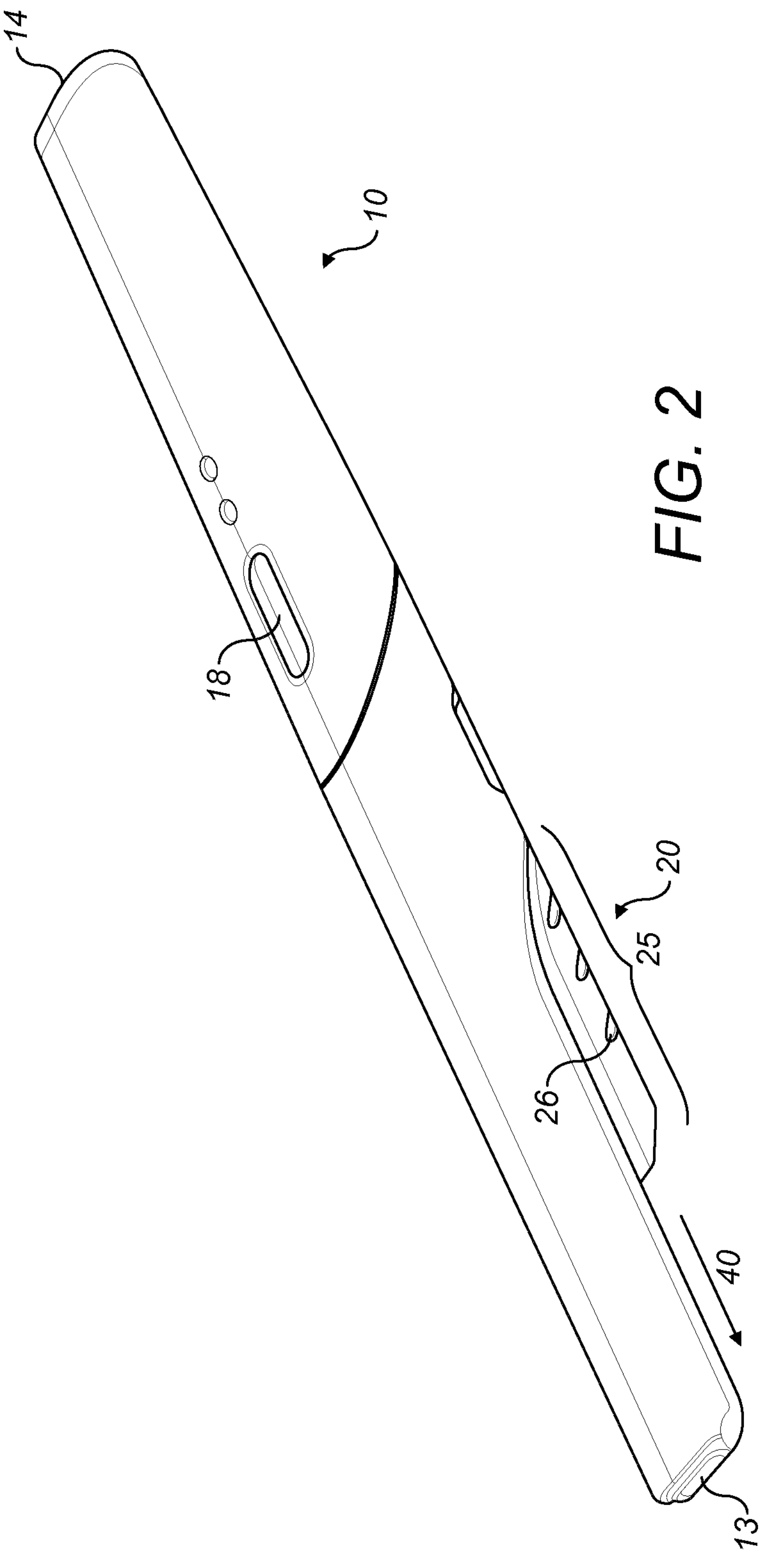

One example of the present invention will now be described with reference to the accompanying drawings, in which:

FIG. 1 shows a bottom perspective view of a separate aerosol generating device and capsule according to the present invention; and FIG. 2 shows am top perspective view of an aerosol generating device according to the present invention with a capsule hosted in the device.

Referring to FIG. 1, an example of an aerosol generating device 10 according to the present invention comprises an elongate body 12 with a first 13 and second 14 end. The aerosol generating device further comprises a cavity 11 positioned on an elongate side of the body 12 between the first 13 and second 14 end. FIG. 1 further shows a capsule 20, configured to contain an aerosol generating substance, according to the present invention, also having an elongate body 22 between a first 23 and second 24 end. The shape of the cavity 11 of the aerosol generating device 10 and the shape of the capsule 20 are configured such that the capsule may be inserted into the cavity 11 of the aerosol generating device 10 along a direction 30 approximately parallel with the elongate axis of the body 12. The capsule may then be hosted in the cavity 11 such that it lies closely along an elongate side of the aerosol generating device 10 and does not extend beyond the first 13 or second 14 ends.

In the exemplary aerosol generating device 10 of FIG. 1, the body 12 of the aerosol generating device 10 has a substantially circular or elliptical cross section along a first portion 15 of its length such that, along this portion 15, the device has an approximately cylindrical shape. The second, remaining portion 16 of the body has a reduced cross sectional area of approximately semi-circular shape. The complete shape of the body 12 can thus be approximated by the remaining volume after removing an approximately semi-cylindrical portion 16 from a partial length of a cylinder. An axially aligned cavity 11 is thus formed in the first cylindrical portion 15 of the device by an opening 11 at the interface between these two portions.

The body 22 of the capsule 20 also has an approximately semi-cylindrical shape with a cross section closely matching that of the axially aligned cavity 11 in the aerosol generating device 10 such that the capsule 10 may be inserted along insertion direction 30 and be retained securely in the cavity 11. The lengths of the cavity 11 and capsule 10 may be chosen such that a portion of the capsule may remain exposed, external to the body 12 of the aerosol generating device 10 but also so that the exposed length is less than the distance between the cavity 11 and first end 13 of the device such that no part of the capsule 11 extends past the first end 13 of the device when hosted.

As shown in FIG. 2, this configuration results in the hosted capsule 20 lying closely against the body 12 of the aerosol generating device and therefore the capsule does not substantially extend the dimensions of the device in any one direction. That is, the hosted capsule, although partially external to the body of the aerosol generating device, lies within the volume defined by the length and maximum cross section of the aerosol generating device.

Although an approximately cylindrical shaped assembly has been used to illustrate this concept, it will be clear that any other appropriate shape may be chosen for the body 12 of the aerosol generating device, the capsule 20 and the cavity 11, such that the hosted capsule lies against the body of the aerosol generating device in this way.

A portion 25 of the capsule shell may be constructed from transparent material such that the amount of aerosol generating substance remaining within the capsule may be visually gauged by a user. The transparent portion 25 may also substantially correspond to the portion of the capsule that is exposed when it is hosted in the device, as shown in FIG. 2. In this way, a user may equally visually gauge the remaining aerosol generating substance within the capsule when the capsule is hosted in the cavity of the aerosol generating device. Such an arrangement provides a much more cost effective option than providing transparent windows embedded or engraved in the body of the aerosol generating device itself in order to see through to gauge the remaining liquid contained within.

Since a portion of the capsule 25 is exposed when hosted in the cavity, the capsule 10 may be simply removed by applying a force against the capsule in a direction 40 opposite to the insertion direction. This process may be facilitated by an array of ridges 26 disposed on the outward facing surface of the exposed capsule portion 25 forming a grip to which a lateral force may be applied. This provides a user-friendly capsule removal procedure which may be achieved simply using one hand.

The aerosol generating device may further comprise a retention means (not shown) disposed within the cavity 11, such as a clip mechanism, to further secure the capsule when hosted in the cavity 11. The aerosol generating device may further be provided with a corresponding release means, such as a capsule release button 17, configured to release the retention means such that the capsule may be removed by a user-applied force to the capsule. Alternatively it may be partially ejected by the release of a biased spring component when the button 17 is pressed.

The aerosol generating device may further comprise a mouthpiece 19, an internal heater assembly (not shown), a power source such as a battery occupying part of the first portion of the device 15 and providing power to the heater assembly, a substance transfer means configured to draw an aerosol generating substance to the heater and a heater control means activated by a button 18 on the body of the aerosol generating device.

The substance transfer means may further include an inlet valve at the base of the cavity 11 in fluidic connection to the heater assembly. The inlet valve may be configured to engage an outlet at the end 24 of the capsule 20 when hosted in the cavity 11. Therefore, when a user inserts the capsule 20 into the cavity 11, the outlet of the capsule engages the inlet valve of the substance transfer means, forming a channel between the capsule and heater assembly through which an aerosol generating substance may be drawn. Thus, by drawing on the mouthpiece 13 whilst activating the heater control button 18, the aerosol generating substance is delivered to the activated heater assembly producing an aerosol that may be inhaled by the user through the mouthpiece 13.

The provision of the cavity 11 on the side of the device 20 means that the ends 13, 14 are left free to facilitate use with one or more of the above components. For example, the mouthpiece may be placed at one end 13 and the battery may be replaced through the second end 14, which is not possible in prior art devices in which a cartridge is attached to one of the ends of the device.

The aerosol generating device according to the present invention may further comprise recognition means configured to read capsule type information provided by the capsule when hosted in the cavity. This capsule type information may include the type of aerosol generating substance contained within the capsule and the specific heating parameters (such as temperature and duration of heating) to be used. In this way, the appropriate heating parameters for the specific substance contained in the capsule 20 may be applied by the aerosol generating device 10 to provide an optimally produced aerosol to the user.

The capsule type information may be encoded onto the capsule in the number, size and/or spatial distribution of the gripping ridges 26 provided on the capsule shell. The recognition means of the aerosol generating device may then comprise a pressure sensitive region on an inner surface of the cavity configured to read the number and distribution of ridges 26 and interpret this information to apply the correct heating parameters to the corresponding aerosol generating substance.

Although this is one example, the provision of capsule type information on the capsule and recognition means of the aerosol generating device may be realised in a number of different ways to provide the effect of heating settings adapted to the specific aerosol substance contained within the capsule 20. For example chemical marking such as secure ink could be used instead of encoding the information in the gripping means. Furthermore electromagnetic marking such as RFID, NFC or a barcode may be used which may be read by a corresponding recognition means of the aerosol generating device.

The electromagnetic marking means and corresponding recognition means of the device may also be used to send a message, for example to a user's mobile telephone, to provide information on the remaining substance within the capsule or to inform a user that a non-genuine capsule is being used.

The cavity may further comprise (either as part of the recognition means or via alternative components) means to ensure that only the genuine capsule configured to operate with the aerosol generating device may be accepted by the cavity to function with the device. This feature may take the form of specific internal grooves or thread which are configured to only accept the capsule designed for use with the device. Similarly the electromagnetic marking may include a specific signal provided to the heater assembly to permit it to function only with the designated capsule or for it to function in a basic mode when a non-genuine capsule is inserted.

The heater control button 18 may further be provided with fingerprint recognition means such that the heater assembly is only operable when the correct fingerprint is recognised by the button 18, such that a device may only be used by a designated user.

In a further example of the invention, the heating means are provided in the capsule 20 rather than the aerosol generating device 10 such that an appropriate heating assembly to the specific substance may be provided and the heater may be changed regularly and easily with the capsule 20, rather than the aerosol generating device 10 itself requiring regular maintenance. In such an embodiment, the capsule 20 may further comprise electrical connections, configured to engage with those of the battery within the aerosol generating device. The capsule heater may further take the form of a portion of the capsule constructed from a material configured to react to an inductive or conductive heating. In such an example, when inserted into the cavity, the capsule may be pierced by a needle having an internal channel allowing the vapour, generated in the capsule, to pass from the capsule to the mouthpiece of the aerosol generating device with the substance transfer means adapted to the passage of vapour rather than liquid.

The examples of the present invention described above provide an aerosol generating device 10 and capsule 22 configured for use with the device which overcome several of the problems of prior art devices. In particular the capsule is hosted in a cavity 11 on a side of the device such that the ends 13, 14 are free to accommodate further components of the device such as the mouthpiece 19 and removable battery. Importantly, when hosted, the capsule may remain partially exposed, external to the body of the aerosol generating device 10, without substantially extending the mentions of the aerosol generating device 10. Therefore a user may benefit from the advantages of an exposed capsule 20 such as the ability to easily remove and replace the capsule, the possibility of identifying the remaining substance within the capsule through a transparent external portion and leaving a greater proportion of the inner volume free to host a larger battery. These advantages are achieved without the common adverse effects of an external capsule, namely the extended dimensions of the device resulting in a bulky object which is awkward to use. This is achieved since the hosted capsule is wholly contained within a volume defined by the length and maximum width of the aerosol generating device.

The invention claimed is:

1. An aerosol generating device comprising:

an elongate body having a first end and a second end, the elongate body extending around a central longitudinal axis thereof extending between the first and second ends;

an inlet configured to receive an aerosol generating substance in a vaporized state;

a power source; and a cavity positioned on a first elongated side of the elongate body, the cavity defining a central longitudinal axis therein that is laterally offset from the central longitudinal axis of the elongate body, such that an outer surface of the first elongated side is closer to the central longitudinal axis of the cavity than to the central longitudinal axis of the elongate body; wherein the cavity is configured to host a capsule, and the cavity and capsule are configured such that, when the capsule is hosted in the cavity, the capsule forms a portion of the first elongated side of the elongate body and does not extend beyond the first and second ends;

the capsule comprising an external shell configured to contain an aerosol generating substance, the external shell comprising an outlet at an end of the capsule, the outlet configured to engage with the inlet when the capsule is hosted in the cavity, the capsule comprising electrical connections and a heating assembly configured to vaporize the aerosol generating substance inside the capsule;

the inlet is configured to draw the aerosol generating substance in the vaporized state from the capsule; and the electrical connections are configured to connect the heating assembly to the power source when the capsule is hosted in the cavity.

2. The aerosol generating device of claim 1 wherein the cavity and capsule are configured such that, when the capsule is hosted in the cavity, the capsule remains at least partially exposed, external to a body of the aerosol generating device.

3. The aerosol generating device of claim 2 wherein the cavity is arranged such that the capsule is inserted in a direction substantially parallel to the central longitudinal axis of the elongate body.

4. The aerosol generating device of claim 1 further comprising:

a mouthpiece at the first end of the body;

the heater assembly;

a heater control means for selectively supplying power from the power source to the heater assembly;

the inlet for controllably drawing the substance from the capsule through the cavity to the heater assembly; such that, when power is supplied to the heater assembly together with the substance, an aerosol is generated which may be drawn through the mouthpiece.

5. The aerosol generating device of claim 1 further comprising:

retention means for releasably retaining the capsule in the cavity; and release means for releasing the retention means such that the capsule may be removed from the cavity.

6. The aerosol generating device of claim 1 further comprising:

a recognition means configured to read capsule type information associated with the capsule; wherein the capsule type information comprises at least one of a type of aerosol generating substance retained in the capsule;

a heating temperature and a duration of heating to be applied to the substance; and a volume of aerosol generating substance retained in the capsule.

7. A capsule configured for use with an aerosol generating device, the aerosol generating device comprising:

an elongate body having a first end and a second end, the elongate body extending around a central longitudinal axis thereof extending between the first and second ends;

an inlet configured to receive an aerosol generating substance in a vaporized state;

a power source; and a cavity positioned on a first elongated side of the elongate body, the cavity defining a central longitudinal axis therein that is laterally offset from the central longitudinal axis of the elongate body, such that an outer surface of the first elongated side is closer to the central longitudinal axis of the cavity than to the central longitudinal axis of the elongate body, wherein the cavity is configured to host a capsule, and the capsule is configured to contain an aerosol generating substance, and the capsule comprising:

an external shell configured to retain an aerosol generating substance;

an outlet in the external shell configured to engage with the aerosol generating device when the capsule is retained in the cavity, the outlet being at an end of the capsule, the outlet configured to engage with the inlet when the capsule is hosted in the cavity;

electrical connections and a heating assembly configured to vaporize the aerosol generating substance inside the capsule, the inlet being configured to draw the aerosol generating substance in the vaporized state from the capsule, the electrical connections being configured to connect the heating assembly to the power source when the capsule is hosted in the cavity; and identification means configured to be read by a recognition means of the aerosol generating device and provide capsule type information to the aerosol generating device when the capsule is hosted in the cavity, wherein the capsule type information comprises at least one of: a type of aerosol generating substance retained in the capsule, a heating temperature and a duration of heating to be applied to the substance, and a volume of aerosol generating substance retained in the capsule, wherein the identification means is provided by gripping means, the capsule type information being encoded in at least one of: the number of gripping means on the external shell, and the positions of the gripping means relative to a reference point on the external shell, and wherein the cavity and capsule are configured such that, when the capsule is hosted in the cavity, the capsule forms a portion of the first elongated side of the elongate body and does not extend beyond the first and second ends.

8. The capsule of claim 7 wherein a portion of the external shell is transparent such that a substance contained therein is visible to a user, the transparent portion being at least partially exposed when the capsule is hosted in the cavity of the aerosol generating device.

9. The capsule of claim 7 further comprising gripping means arranged on the external shell, the gripping means configured so as to improve the ease with which the user may apply a required force to the capsule in order to remove the capsule from the cavity of the aerosol generating device.

10. The capsule of claim 7 wherein part of the capsule is made of a material configured to conduct heat or configured to react to an induction current.

11. The aerosol generating device of claim 4 wherein the cavity is arranged such that the capsule is inserted in a direction substantially parallel to the central longitudinal axis of the elongate body.

12. A kit comprising:

an aerosol generating device including an elongate body having a first end and a second end, the elongate body extending around a central longitudinal axis thereof extending between the first and second ends, an inlet configured to receive an aerosol generating substance in a vaporized state, a power source, and a cavity positioned on a first elongated side of the elongate body, the cavity defining a central longitudinal axis therein that is laterally offset from the central longitudinal axis of the elongate body, such that an outer surface of the first elongated side is closer to the central longitudinal axis of the cavity than to the central longitudinal axis of the elongate body; and a capsule including an external shell configured to retain an aerosol generating substance, and an outlet in the external shell configured to engage with the aerosol generating device when the capsule is retained in the cavity, the outlet being at an end of the capsule, the outlet configured to engage with the inlet when the capsule is hosted in the cavity, the capsule comprising electrical connections and a heating assembly configured to vaporize the aerosol generating substance inside the capsule, the inlet being configured to draw the aerosol generating substance in the vaporized state from the capsule, the electrical connections being configured to connect the heating assembly to the power source when the capsule is hosted in the cavity;

wherein the cavity is configured to host the capsule, and the cavity and capsule are configured such that, when the capsule is hosted in the cavity, the capsule forms a portion of the first elongated side of the elongate body and does not extend beyond the first and second ends.

* * * * *